United States Patent
John et al.

(10) Patent No.: US 9,874,714 B2
(45) Date of Patent: Jan. 23, 2018

(54) ADJUSTABLE STAND FOR AN OPTICAL OBSERVATION INSTRUMENT

(71) Applicant: KARL KAPS GMBH & CO. KG, Asslar (DE)

(72) Inventors: Mathias John, Schöffengrund (DE); Joachim Luber, St. Margrethen (CH)

(73) Assignee: KARL KAPS GMBH & CO. KG, Asslar (DE)

( * ) Notice: Subject to any disclaimer, the term of this patent is extended or adjusted under 35 U.S.C. 154(b) by 9 days.

(21) Appl. No.: 15/025,786

(22) PCT Filed: Sep. 29, 2014

(86) PCT No.: PCT/EP2014/002645
§ 371 (c)(1),
(2) Date: Mar. 29, 2016

(87) PCT Pub. No.: WO2015/043763
PCT Pub. Date: Apr. 2, 2015

(65) Prior Publication Data
US 2016/0238815 A1    Aug. 18, 2016

(30) Foreign Application Priority Data
Sep. 30, 2013  (DE) .................. 10 2013 016 369

(51) Int. Cl.
*G02B 21/00*   (2006.01)
*G02B 7/00*    (2006.01)
(Continued)

(52) U.S. Cl.
CPC .............. *G02B 7/001* (2013.01); *A61B 90/25* (2016.02); *F16M 11/08* (2013.01); *F16M 11/10* (2013.01);
(Continued)

(58) Field of Classification Search
CPC ........ F16M 11/00; F16M 11/02; F16M 11/04; F16M 11/041; F16M 11/043;
(Continued)

(56) References Cited

U.S. PATENT DOCUMENTS

| 5,480,114 | A | * | 1/1996 | Nakamura | ........... F16M 11/126 248/123.2 |
| 5,492,296 | A | * | 2/1996 | Biber | ..................... G02B 7/001 248/292.13 |
| 2002/0014562 | A1 | * | 2/2002 | Twisselmann | ......... F16M 11/18 248/123.11 |

FOREIGN PATENT DOCUMENTS

| DE | 4231516 A1 | 3/1994 |
| DE | 9219240 U1 | 9/2011 |

(Continued)

*Primary Examiner* — Arnel C Lavarias
(74) *Attorney, Agent, or Firm* — Abelman, Frayne & Schwab

(57) ABSTRACT

An adjustable stand having a first spindle, a second spindle and a flange for connection to and positioning of an optical observation instrument. Positioning of the instrument relative to the stand is maintained by a torque compensation device respectively arranged with at least one of the spindles to compensate against torque caused by the mass and positioning of the instrument and spindles. Each torque compensation device includes a brake for securing the spindle, a spring, a motor for adjusting the spring tension, and a motor controller which includes a transmission device with a transmission ratio deviating from 1:1 and which is positioned between the spring and the spindle. The motor controller controls the spring tension by selectively rotating the motor based on instructions from a control unit, which receives signals from a spindle-position sensor and a spring-tension sensor and automatically provides counter-torque rotational movement instructions to the motor controller.

25 Claims, 1 Drawing Sheet

(51) Int. Cl.
*F16M 11/10* (2006.01)
*F16M 11/18* (2006.01)
*F16M 11/20* (2006.01)
*G02B 21/24* (2006.01)
*A61B 90/25* (2016.01)
*F16M 11/08* (2006.01)
*F16M 13/02* (2006.01)

(52) U.S. Cl.
CPC ........... *F16M 11/105* (2013.01); *F16M 11/18* (2013.01); *F16M 11/2021* (2013.01); *F16M 13/027* (2013.01); *G02B 21/0012* (2013.01); *G02B 21/24* (2013.01); *F16M 2200/021* (2013.01); *F16M 2200/041* (2013.01); *F16M 2200/044* (2013.01)

(58) Field of Classification Search
CPC .. F16M 11/045; F16M 11/046; F16M 11/048; F16M 11/06; F16M 11/08; F16M 11/10; F16M 11/105; F16M 11/12; F16M 11/121; F16M 11/123; F16M 11/125; F16M 11/126; F16M 11/128; F16M 11/18; G02B 21/00; G02B 21/0012; G02B 21/24
USPC ....... 359/362, 363, 368, 369, 372, 374, 375, 359/376, 384; 248/550, 560, 561, 562, 248/563, 567, 575, 580, 581, 582, 583, 248/364
See application file for complete search history.

(56) References Cited

FOREIGN PATENT DOCUMENTS

| | | |
|---|---|---|
| EP | 0656194 A1 | 6/1995 |
| EP | 1312850 A2 | 5/2003 |
| JP | h06-269463 A | 9/1994 |
| JP | H08-266555 A | 10/1996 |
| JP | H09-182759 A | 7/1997 |
| JP | 2009201995 A | 9/2009 |

\* cited by examiner

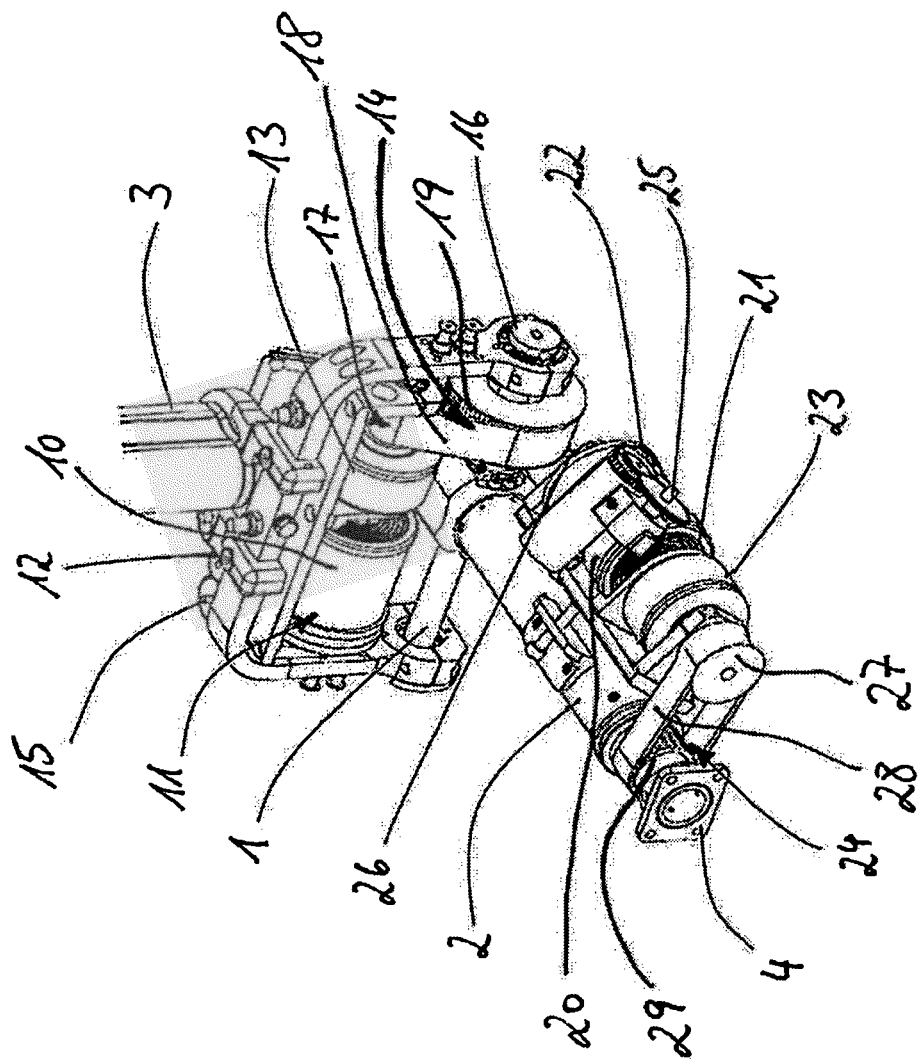

ADJUSTABLE STAND FOR AN OPTICAL OBSERVATION INSTRUMENT

CROSS REFERENCE TO RELATED APPLICATION

This application claims benefit under 35 U.S.C. § 371 to international application No. PCT/EP2014/002645, filed on Sep. 29, 2014, which claims priority to German application no. DE 102013016369.2, filed Sep. 30, 2013, the contents of which are incorporated by reference in their entireties.

The invention relates to an adjustable stand for an optical observation instrument, in particular for a surgical microscope, with a tilt spindle and with a swivel spindle for the optical observation instrument and with a flange for connection to the optical observation instrument.

It is known that torque compensation becomes necessary for the delicate and precise movement of a surgical microscope during which the torques vary, for example by addition of an optional device. Complex systems attempt to compensate each of the movement spindles, as shown for example in JP 9182759 A. There, compensation is effected, also partially automatically, by shifting weights. A disadvantage is that this apparatus is very expensive and therefore can also only be used for high-end systems.

This is to be assessed similarly in the case of the further solutions known from the state of the art according to JP 8266555 A, JP 6269463 A and EP 0 656 194 A1.

More economical torque compensation devices which are attached directly to the surgical microscope, and not to its support, are known for example from DE 42 31 516 A1, EP 1 312 850 A2 or JP 2009201995 A.

In the case of DE 42 31 516 A1 one or more spindles are torque-compensated by a manually adjustable spring. This device can only be used in the case of small torque variations and the system has to be readjusted manually depending on the position of the spindle. Today's microscopes have more and more accessories. In order to compensate for this additional torque, the size of the system named here would have to be increased to the extent that its use is no longer possible in practice.

A different approach is adopted in EP 1 312 850 A2. Here, a gas pressure spring and a converter which converts the linear pressure of the gas pressure spring or also spring elements to a counter-torque for torque compensation of the microscope are used. The disadvantage of this device is the installation size necessary for it, as well as the lack of possibility for setting the torque compensation automatically or semi-automatically.

JP 2009201995 A describes a different approach. Here, with the help of two linear drives, the microscope is manually adjusted in the x and y direction relative to the suspension on the support system, until torque compensation takes place. The great disadvantage of this invention is that the microscope is thereby adjusted to this extent from the centre and the focal point of the microscope deviates more and more during rotational movements. Furthermore, in principle no automatic or semi-automatic torque compensation is possible with this device.

The object of the present invention is therefore to provide a simple and economical torque-compensation solution for an optical observation instrument, in particular a surgical microscope which, despite the wide torque compensation range due to more and more accessories, features only a small installation space.

This and other objects are achieved by an adjustable stand having a first (e.g., tilt) spindle, a second (e.g., swivel) spindle, and a flange for connection to and positioning of an optical observation instrument. Positioning of the optical observation instrument relative to the adjustable stand is maintained by a pair of torque compensation devices, each of which being arranged with one of the spindles. The torque compensation devices compensate against torque forces which tend to cause undesirable rotation of the spindles due to the mass and positioning of the optical observation instrument and the spindles. Each spindle torque compensation device includes a brake for securing the spindle, a spring, a motor for adjusting tension of the spring, and a motor controller that includes a torque transmission device with a transmission ratio deviating from 1:1 and which is positioned between the spring and the spindle. The motor controller controls tension on the spring by selectively rotating the motor based on instructions from a control unit, which receives signals from a spindle position sensor and a spring tension sensor and automatically provides counter-torque rotational movement instructions to the motor controller.

In an embodiment of the first torque compensation device associated with the first spindle, two sensors, which detect the positioning of the first spindle and spring tension of the first spring, send electronic signals to a control unit to automatically provide instructions to the first control motor to control counter-torque rotational movement of the first spindle. As the first spring is connected to a first motor, the spring tension of the first spring need not be set manually, which makes the operator's work substantially easier. Automatic setting of the counter-torque in the first spring, which can be determined in the control unit by means of a suitable algorithm, can be effected on the basis of a motor-driven rotation of the first spring. The motor controller is operated by the control unit on the basis of the result of the assessment by the two sensors. The first brake serves to secure the device in the selected position, with the result that, even in the event that no torque compensation has taken place, the burden on the operator is relieved and there is also no inadvertent movement of the surgical microscope. The transmission of the counter-torque built up in the first spring to the first spindle which is acted on by the torque is effected via the first torque transmission device. Because the first torque compensation device is arranged on the first spindle, a very compact, space-saving design is obtained.

An advantageous development of the invention provides that on the second spindle a second torque compensation device is arranged, which basically has the same components as those of the first torque compensation device. This also leads to the advantages set out in the previous paragraph, with respect to the second spindle. Because a torque compensation device is arranged on each of the two spindles, the operator enjoys the advantages named above with every possible modification of the optical observation instrument.

A further advantageous development of the invention provides that the tilt spindle is substantially perpendicular to the swivel spindle. As this is the normal formation of these two spindles on the commercially available stands, the device according to the invention can be used thereon.

A further advantageous development of the invention provides that the first torque transmission device and/or the second torque transmission device has a transmission ratio that deviates from 1:1, in particular lies between 1:1.5 and 1:4, and is preferably 1:3. It is thereby possible to minimize the required counter-torques in the spring, for example due to solid accessories that are optionally arranged relatively far from the respective spindle, which then, again, leads to a compact design because of the reduced size of the first spring and first brake.

A further advantageous development of the invention provides that the first brake is connected to a first brake controller and/or the second brake is connected to a second brake controller. Semi-automatic or fully automatic balancing of the device can thereby be achieved, as the brake is automatically released only for the period during which the compensation of the torque acting on the respective spindle is carried out.

A further advantageous development of the invention provides that the first motor controller and/or the second motor controller and/or the first brake controller and/or the second brake controller is contained on a computer as software. This results in the compactness of the device, and all the required controllers can be combined in a single instrument.

A further advantageous development of the invention provides that the axis of the first brake and the axis of the first spring coincide and/or the axis of the second brake and the axis of the second spring coincide. A compact design can thereby be achieved and optimum transmission of the force of the respective motor to the associated spring is guaranteed.

A further advantageous development of the invention provides that the first brake and/or the second brake is an electromagnetic brake. Such brakes can be well controlled, are compact in design and, as standard parts, are inexpensive to use.

A further advantageous development of the invention provides that a surgical microscope or a further member of the stand is attached to the flange. This represents a main application case of the stand according to the invention, with the result that the operator of the surgical microscope enjoys all the advantages named above. The invention is designed such that, instead of the flange for connecting a surgical microscope shown in the embodiment example, a further member of the adjustable stand can be connected.

A further advantageous development of the invention provides that the adjustable stand is a component part of a ceiling, wall or floor stand. It is thereby possible to use commercially available ceiling, wall or floor stands, to the tilt spindle and/or swivel spindle of which the component parts according to the invention can be attached or which can accordingly be retrofitted. This means that it is not necessary to provide expensive attachments—as known from the state of the art—for the ceiling, wall or floor stand that is in any case necessary. This contributes to a more compact design of the whole instrument and in addition saves costs compared with an expensive attachment.

Further advantages and details of the invention are explained with reference to the embodiment represented in the figure. The single figure shows:

a section of an embodiment of an adjustable stand according to the invention.

The figure shows an embodiment of an item according to the invention in the form of a part of a ceiling stand for a surgical microscope. The ceiling stand is represented here only with its connecting piece 3; however, it is well known to a person skilled into the art, with the result that further details can be dispensed with here, in particular in view of the fact that the design of the other part of the ceiling stand is unimportant for the invention. Other types of stand, such as wall or floor stands, can equally well be used within the framework of the invention.

Two spindles, a tilt spindle 1 and a swivel spindle 2, are formed at the end of the connecting piece 3. At the free end of the swivel spindle 2 a flange 4 is formed, to which the surgical microscope (not shown) or a further member of the ceiling stand can be attached. Any surgical microscope can be attached to the flange 4; this also applies to accessory parts that can be attached to the surgical microscope. The surgical microscope need not be attached directly to the flange 4, but a further member or several members of the ceiling stand can also be arranged between the flange 4 and the surgical microscope.

In the figure the tilt spindle 1 runs horizontally; as does the swivel spindle 2, which is aligned orthogonal to it. As a rule, an operator using the surgical microscope has to bring the latter into different positions during an operation. As the centre of gravity of the surgical microscope with accessory parts does not as a rule lie on the swivel spindle 2 and in no case on the tilt spindle 1, there are torques about these two spindles 1, 2. In order that the surgical microscope with its accessories does not rotate about the respective spindle 1, 2 until its centre of gravity comes to lie vertically below the respective spindle 1, 2, counter-torques have to be applied to the respective spindle 1, 2, which compensate for the respective torque due to the position and mass of the surgical microscope together with accessory parts.

Firstly, the mode of operation of the device according to the invention for the tilt spindle 1 is described. Because of the centre of mass of the surgical microscope together with accessory parts and additionally the parts belonging to the swivel spindle 2, the tilt spindle 1 is acted on by a torque, which acts in the anticlockwise direction when the tilt spindle 1 is viewed from the right in the figure. This torque would result in the surgical microscope together with accessory parts and the swivel spindle 2 rotating about the tilt spindle 1 in the anticlockwise direction until the centre of gravity of the system consisting of surgical microscope, accessory parts and swivel spindle 2 is situated vertically below the tilt spindle 1. However, as the operator regularly requires a different position for the surgical microscope in order to be able to work, a corresponding counter-torque—in the clockwise direction, when the tilt spindle 1 is viewed from the right—has to be applied to the tilt spindle 1. This is achieved by attaching a first torque compensation device directly to the tilt spindle 1.

This first torque compensation device has the following component parts that are essential to the invention: a first spring 11, a first motor 12, a first brake 13, a first torque transmission device 14, a first force sensor 15 and a first position sensor 16. The further component parts represented in the figure are not essential to the basic principle of the invention and, in the light of the following description with respect to the parts essential to the invention, their interaction and their arrangement with respect to each other, a person skilled in the art knows how he must form them.

The first sensor 16 is arranged on the tilt spindle 1 at the right-hand end. It ascertains the position and angular position of the tilt spindle 1 in space. The respective present value is transmitted to a computer (not shown). A data cable (not shown) is regularly used for the transmission. However, wireless transmission of these data to the computer is also possible. If a torque acts on the tilt spindle 1 and the first brake 13 is released, the position of the tilt spindle 1 in space varies, at least as regards its angular position. From the time-related variation in the position of the tilt spindle 1 after the release of the first brake 13, which is achieved with reference to the data transmitted from the first position sensor 16, the torque acting can be deduced based on a physical formula known to a person skilled in the art—if he knows the further parameters of the whole system. This is effected by means of a suitable algorithm on the computer. The respective torque is compensated for by the first torque transmission device 14. The latter has the first spring 11 for this purpose. In the embodiment this is a spiral spring which is secured by one end to a first housing 10 and by the other end to a first central shaft, which is not shown. The first motor 12 is connected to the first spring 11 via a suitable force transmission device, for example a pinion, so that its first housing 10 can be rotated with respect to its first central shaft. Further details of the power transmission devices follow below.

The tension of the first spring 11, and thus the force acting through it on the first central shaft, is detected by means of the first force sensor 15. Here the first force sensor 15 detects the angular position of the first central shaft with respect to the first housing 10 of the first spring 11—the spring force of the first spring 11 results from the rotation angle of the first housing 10 driven by the first motor 12 with respect to the first central shaft. The value of the angular position is transmitted to the computer. Here too, a data cable (not shown) is regularly used, but wireless transmission is also possible. If the characteristics of the first spring 11 are known, the force existing in this position can be deduced based on the angular position of the first central shaft with respect to the first housing 10 of the first spring 11. This is done by means of a suitable algorithm within the computer; this is described by a physical formula which is known to a person skilled in the art. Alternatively the first motor 12 could also turn the first central shaft, in order to vary the counter-torque; then too, the first force sensor 15 would detect the angular position of the first central shaft with respect to the first housing 10—only the first central shaft would then be actively rotated by the first motor 12, and not the first housing 10.

For compensation of the torque which acts on the tilt spindle 1 because of the surgical microscope together with accessory parts and swivel spindle 2, the spring force of the first spring 11 is set by means of the first motor 12 such that a counter-torque acts on the tilt spindle 1, which counter-torque acts in the opposite way to the torque and is just as great in magnitude. This occurs in that the first torque transmission device acts on the first central shaft of the first spring 11 and transmits the force of the first spring 11 to the tilt spindle 1 by suitable means. In the embodiment this is effected by a first input toothed wheel 17, which is arranged on the first central shaft of the first spring 11 and transmits the force to the tilt spindle 1 via a first toothed belt 18 to a first output toothed wheel 19, which is arranged on the tilt spindle 1. In the embodiment a transmission ratio of 1:3 is used, so that the relatively high torques which act on the tilt spindle 1, as the lever arm based on the swivel spindle 2 is large, can be compensated for by a first torque compensation device which is as compact as possible. However, the just-named transmission ratio is in no case compulsory and can also assume any other value allowing a small enough installation size of the first torque transmission device. Other, alternative power transmission devices are known to a person skilled in the art, with the result that there is no need to explain them in more detail here.

In order to be able to secure the surgical microscope in a position desired by the operator, a first brake 13 is arranged around the first central shaft of the first spring 11. In the embodiment this is an electromagnetic brake, which is well known to a person skilled in the art and thus need not be described further. Other types of brakes which are known to a person skilled in the art can also be used. The first central shaft is blocked in the closed state by means of this first brake 13, with the result that the tilt spindle 1 is blocked via the first toothed belt 18 of the first torque transmission device 14. Only when the operator moves the surgical microscope into a different position does the first brake 13 have to be released, so that the movement can take place and, at the same time, compensation can be effected for the modified torque acting on the tilt spindle 1 because of the varied position of the system consisting of surgical microscope together with accessory parts and swivel spindle 2, by means of an adapted counter-torque.

The functionality and mode of operation with respect to the swivel spindle 2 are the same in principle as stated above with respect to the tilt spindle 1. Therefore, the following only briefly explains again, in summary, what component parts are arranged, and how with respect to each other, and what function they perform. The only difference in principle is the design of the second torque transmission device 24. In this case a transmission in the ratio 1:3 is not selected, but there is a ratio of 1:1. This follows from the fact that smaller torques resulting from the centre of mass of the surgical microscope together with accessory parts act on the swivel spindle 2, as the lever arm here is significantly shorter—there is no intermediate spindle, unlike what is stated above in the description relating to the tilt spindle 1; there, this was the swivel spindle 2. Thus the ratio of 1:1 is enough to still be able to attach a compact second torque compensation device.

The second torque compensation device comprises a second spring 21 in the form of a spiral spring, which is secured by its first end to a second housing 20 and by its second end to a second central shaft (not shown) of the second spring 21. At its free end the second central shaft has a second input toothed wheel 27 which, via a second toothed belt 28, transmits the force from the second central shaft to the swivel spindle 2 to a second output toothed wheel 29. These two toothed wheels 27, 29 together with the toothed belt 28 form a second torque transmission device 24. Around the second central shaft of the second spring 21 a second electromagnetic brake 23 is arranged, which can secure the second central shaft. In order to apply force to the second spring 21 the second torque compensation device has a second motor 22 which cooperates with the housing of the second spring 21 via a pinion.

In addition a second force sensor 25 and a second position sensor 26 are present, which have the same functions with respect to the swivel spindle 2 as their counterparts on the first torque compensation device.

The device according to the invention can be operated in different modes. In a first mode, with the brakes 13, 23 released, the surgical microscope is moved into a different position until the position in which the operator wishes to work is reached. In this position the positions of the tilt spindle 1 and the swivel spindle 2 are determined by means of the position sensors 16, 26—as already stated above—and the two motors 12, 22 can then be controlled by the operator by means of keys until the whole system is balanced. Once this balanced state is achieved, the tilt spindle 1 and the swivel spindle 2 are blocked by the operator by means of the two brakes 13 and 23, with the result that the operator, even if he pushes against the surgical microscope, cannot inadvertently modify the position of the surgical microscope.

A balanced state at a position of the tilt spindle 1 and the swivel spindle 2 can also be effected automatically, instead of adjustment via keys.

In a second mode the two brakes 13, 23 are automatically released for a predetermined short time at the current position of the tilt spindle 1 and swivel spindle 2, with the result that the modified torques rotate the tilt spindle 1 and the swivel spindle 2. Because of the time-related variations of the tilt spindle 1 and the swivel spindle 2, which are detected by the first position sensor 16 and second position sensor 26 respectively, these values can be converted by the algorithms already mentioned above, such that the variation to be applied to the respective spring stiffness of the springs 11, 21 can be calculated and the adjustment can be carried out automatically via the two motors 12, 22. As soon as this has taken place, the two brakes 13, 23 are reactivated, with the result that the tilt spindle 1 and the swivel spindle 2 are blocked in the position which the operator has pre-set.

Once such a balanced position exists, the relevant parameters of the two position sensors 16, 26 and the two force sensors 15, 25 can be stored and determined with reference to the abovementioned parameters of the respective system required for the calculation of the torques, depending on the surgical microscopes used together with—in each case interchangeable—accessory parts. Once such a balanced state has been reached, it is possible hereafter, with reference to the data obtained for each further position approached by the operator with the surgical microscope, for automatic torque compensation to be effected in a third mode during use. This is effected by bringing the surgical microscope into the new position after the brakes 13, 23 are released by the operator. There the two brakes 13, 23 are reactivated, with the result that the tilt spindle 1 and the swivel spindle 2 are again blocked. Based on the data from the two position sensors 16, 26, both the variation of the position of the tilt spindle 1 and the swivel spindle 2 and the variation of their angular position can be determined. As the system was balanced before variation of the position, a new position and thus a new counter-torque can now be calculated on the basis of the new data obtained and the known mechanical data. The newly calculated counter-torque is now transmitted, by operation of the two motors 12, 22, to the two springs 11, 21 by varying their respective tension. The corresponding counter-torque is then transmitted to the tilt spindle 1 and the swivel spindle 2 via the two torque transmission devices 14, 24.

A disadvantage of the third mode described above is that the operator has to exert a relatively high force when modifying the position as, on the displacement path from the old position into the new position, he receives no support through torque compensation. Rather, this only takes place for balancing in the final position pre-set by the operator. This problem is solved in that in a fourth mode an automatic torque compensation is carried out during the displacement. To this end, throughout the entire movement from the initial position to the final position the variation of the position and angular position of the tilt spindle 1 and the swivel spindle 2 are constantly detected via the two position sensors 16, 26 and transmitted to the computer. The latter then constantly determines, by means of the algorithms already mentioned above, how the counter-torque in the respective spring 11, 21 needs to be varied by means of the motors 12, 22 in order to have a balanced system. By means of the balancing of the entire system present in each intermediate position—the torque is opposed equally to the applied counter-torque—the operator can accomplish the entire movement from the initial position to the final position of the surgical microscope with very little effort. After the final position is reached, the two brakes 13, 23 are again blocked, so that the operator can work in this position and inadvertent touching of the surgical microscope cannot lead to a modification of its position.

LIST OF REFERENCE NUMBERS 1 tilt spindle
2 swivel spindle
3 connecting piece
4 flange
10 first housing
11 first spring
12 first motor
13 first brake
14 first torque transmission device
15 first force sensor
16 first position sensor
17 first input toothed wheel
18 first toothed belt
19 first output toothed wheel
20 second housing
21 second spring
22 second motor
23 second brake
24 second torque transmission device
25 second force sensor
26 second position seas
27 second input toothed wheel
28 second toothed belt
29 second output toothed wheel

The invention claimed is:

1. An adjustable stand for an optical observation instrument comprising:
a first spindle, a second spindle, and a flange for connection to the optical observation instrument or a further member of the adjustable stand;
a first torque compensation device configured to control rotation of the first spindle includes a first brake for securing the first spindle, a first spring, a first motor for adjusting spring tension of the first spring, and a first motor controller having a first torque transmission device with a transmission ratio that deviates from 1:1, the first torque transmission device being positioned between the first spring and the first spindle to selectively rotate the first spindle; a first position sensor for determining the position of the first spindle and a first force sensor for determining the spring tension of the first spring, wherein the first position sensor and the first force sensor are connected to a control unit which controls the first motor controller.

2. The adjustable stand according to claim 1, wherein the second spindle comprises
a second torque compensation device configured to control rotation of the second spindle includes a second brake for securing the second spindle, a second spring, a second motor for adjusting spring tension of the second spring, and a second motor controller having a second torque transmission device with a transmission ratio that deviates from 1:1, the second torque transmission device being positioned between the second spring and the second spindle to selectively rotate the second spindle; a second position sensor for determining the position of the second spindle and a second force sensor for determining the spring tension of the second spring, wherein the second position sensor and the second force sensor are connected to the control unit which controls the second motor controller.

3. The adjustable stand according to claim 1, wherein the first spindle is substantially perpendicular to the second spindle.

4. The adjustable stand according to claim 2, wherein at least one of the transmission ratios of the first and second torque transmission devices is in a range between 1:1.5 and 1:4.

5. The adjustable stand according to claim 2, wherein at least one of the first brake is connected to a first brake controller, and the second brake is connected to a second brake controller.

6. The adjustable stand according to claim 5, wherein at least one of the first motor controller, the second motor controller, the first brake controller, and the second brake controller include programming code stored in a memory device and executable by a processor of a computer device.

7. The adjustable stand according to claim 2, wherein at least one of an axis of the first brake and an axis of the first spring coincide, and an axis of the second brake and an axis of the second spring coincide.

8. The adjustable stand according to claim 2, wherein at least one of the first brake and the second brake is an electromagnetic brake.

9. The adjustable stand according to claim 1, wherein a surgical microscope or a further member of the stand is attached to the flange of the adjustable stand.

10. The adjustable stand according to claim 1, wherein the adjustable stand is a component part of a ceiling, wall or floor stand.

11. The adjustable stand according to claim 1, wherein the first brake is connected to a first brake controller.

12. The adjustable stand according to claim 1, wherein the first motor controller includes programming code stored in a memory device and executable by a processor of a computer device.

13. The adjustable stand according to claim 2, wherein at least one of the first motor controller and the second motor controller include programming code stored in a memory device and executable by a processor of a computer device.

14. The adjustable stand according to claim 1, wherein an axis of the first brake and an axis of the first spring coincide.

15. The adjustable stand according to claim 1, wherein the first brake is an electromagnetic brake.

16. The adjustable stand according to claim 1, wherein the transmission ratio of the first torque transmission device is 1:3.

17. The adjustable stand according to claim 2, wherein at least one of the transmission ratios of the first torque transmission device and the second torque transmission device is 1:3.

18. The adjustable stand according to claim 1, wherein the optical observation instrument is a surgical microscope.

19. The adjustable stand according to claim 2, wherein the optical observation instrument is a surgical microscope.

20. The adjustable stand according to claim 1, wherein the control unit, in response to electronic signals from the first force and spring tension sensors, automatically determines required counter-torque rotational movement for the first spindle and sends corresponding electronic commands to the first motor controller.

21. The adjustable stand according to claim 2, wherein the control unit, in response to electronic signals from the second force and spring tension sensors, automatically determines required counter-torque rotational movement for at least one of the first and second spindles and sends corresponding electronic commands to at least one of the first and second motor controllers.

22. The adjustable stand according to claim 1, wherein the first spindle and the second spindle are respectively one of a tilt swivel or a swivel spindle.

23. The adjustable stand according to claim 2, wherein the first spindle and the second spindle are respectively one of a tilt swivel or a swivel spindle.

24. The adjustable stand according to claim 2, wherein a surgical microscope or a further member of the stand is attached to the flange of the adjustable stand.

25. The adjustable stand according to claim 2, wherein the adjustable stand is a component part of a ceiling, wall or floor stand.

* * * * *